United States Patent [19]

Meserol et al.

[11] Patent Number: 4,666,853
[45] Date of Patent: May 19, 1987

[54] SELF-SUFFICIENT INCUBATION ASSEMBLY

[75] Inventors: Peter M. Meserol, Montville; Jesse L. Acker, Rockaway; Janet G. Murnick, Bernardsville; Dean Pappas, Lodi, all of N.J.

[73] Assignee: Personal Diagnostics, Inc., Whippany, N.J.

[21] Appl. No.: 512,122

[22] Filed: Jul. 8, 1983

Related U.S. Application Data

[63] Continuation-in-part of Ser. No. 411,631, Aug. 26, 1982, abandoned, which is a continuation of Ser. No. 238,049, Feb. 25, 1981, abandoned.

[51] Int. Cl.[4] .................. C12M 1/38; C12M 1/22; G01N 1/10; G01N 21/00
[52] U.S. Cl. ............................. 435/290; 356/246; 356/440; 356/442; 435/287; 435/297; 435/299; 435/301; 435/809
[58] Field of Search ............... 435/287, 297, 298, 299, 435/300, 301, 809, 290; 356/246, 440, 442; 436/69

[56] References Cited

U.S. PATENT DOCUMENTS

| | | | |
|---|---|---|---|
| 3,607,099 | 9/1971 | Scordato | 436/69 X |
| 3,660,242 | 5/1972 | Gordon | 435/809 X |
| 3,832,532 | 8/1974 | Praglin | 435/300 X |
| 3,969,879 | 7/1976 | Catarious | 436/69 X |
| 4,090,921 | 5/1978 | Sawamura | 435/809 X |
| 4,207,394 | 6/1980 | Aldridge, Jr. | 435/300 X |
| 4,286,881 | 9/1981 | Janzen | 356/440 |
| 4,301,252 | 11/1981 | Baker | 435/298 X |
| 4,577,970 | 3/1986 | Meserol | 356/440 |

*Primary Examiner*—Sidney Marantz
*Assistant Examiner*—Jeremy Jay
*Attorney, Agent, or Firm*—R. Gale Rhodes, Jr.

[57] ABSTRACT

Self-sufficient incubation assembly for the in vitro cultivation of microorganisms such as bacteria and for being energized by a self-contained energy source, including a heater for heating means, such as a culture growth dish assembly or a cuvette, for receiving a culture growth medium seeded with microorganisms, to a physiological temperature to cultivate the microorganisms, and electrical circuitry which interconnects the heater with the energy source and which includes a temperature control element in intimate physical contact with the seeded culture growth receiving means to cause the temperature of the control element to be substantially the same as the temperature of the medium; the electrical circuit in operation produces heat and due to its intimate physical contact with the means for receiving the seeded culture growth medium supplements the heating of the medium by the heater and the supplementation reduces the total energy required to be supplied by the energy source to cultivate the microorganisms below that which would be required were the electrical circuitry not to be in intimate physical contact with the culture growth receiving means; and optical means are included to provide an external indication of the growth of the microorganisms within the interior of the assembly.

4 Claims, 25 Drawing Figures

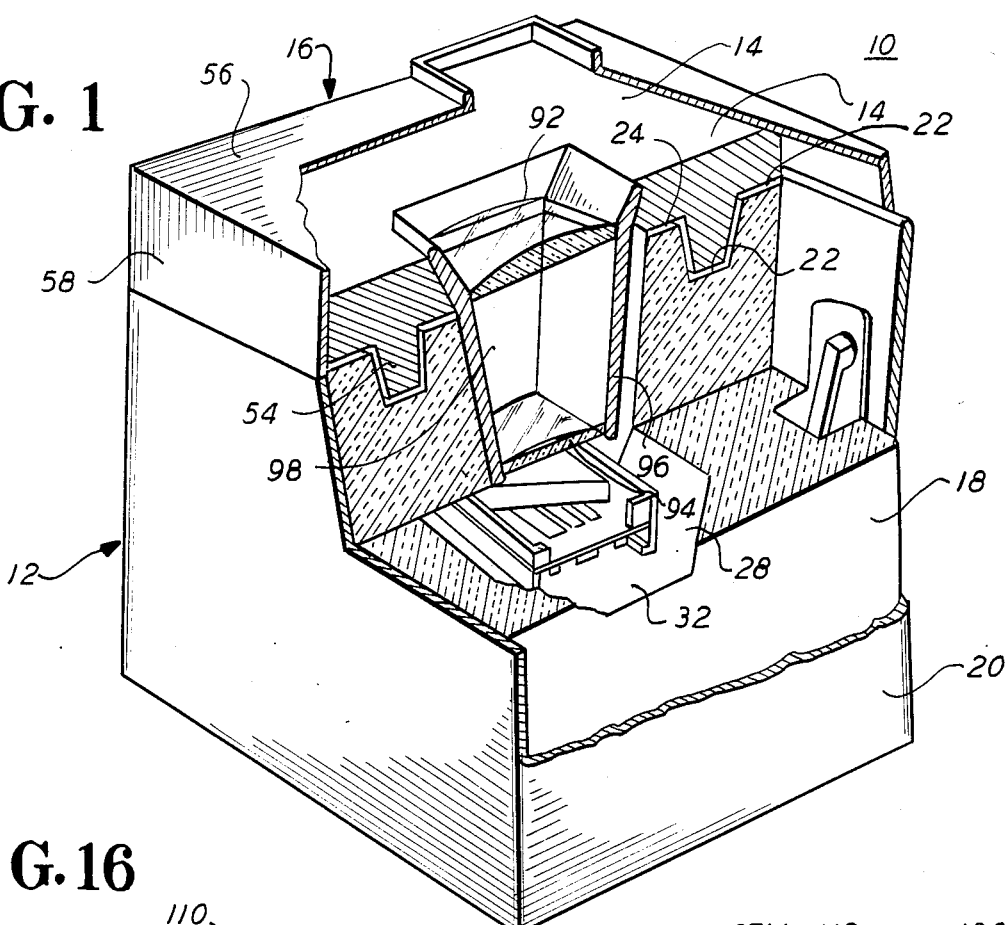
FIG. 1
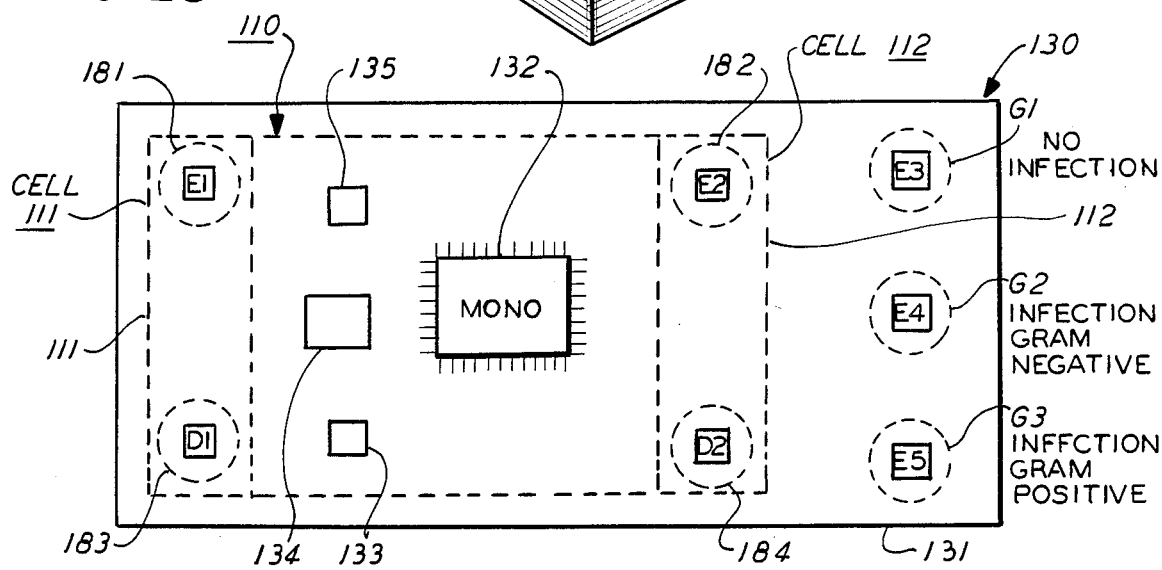
FIG. 16
FIG. 17
DECODER ALGORITHM
1 = CLINICALLY SIGNIFICANT GROWTH
0 = NO CLINICALLY SIGNIFICANT GROWTH
| CUVETTE CELL 111 (G+) | 1 | 0 | 0 | 1 |
|---|---|---|---|---|
| CUVETTE CELL 112 (G-, OR G- AND G+) | 0 | 1 | 0 | 1 |
| OUTPUT LIGHTS | G+ | G- | NO INFECTION | G+ |

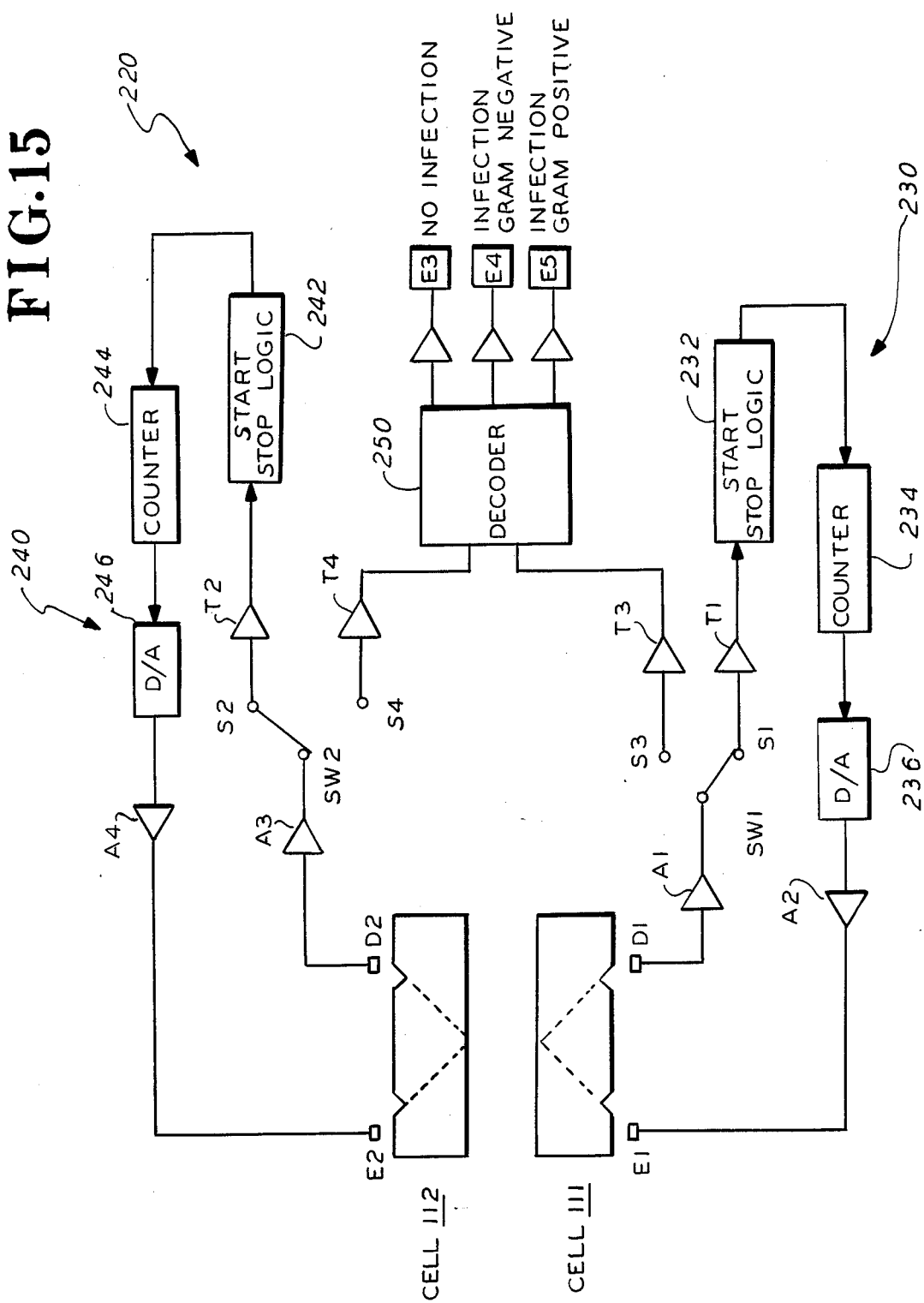

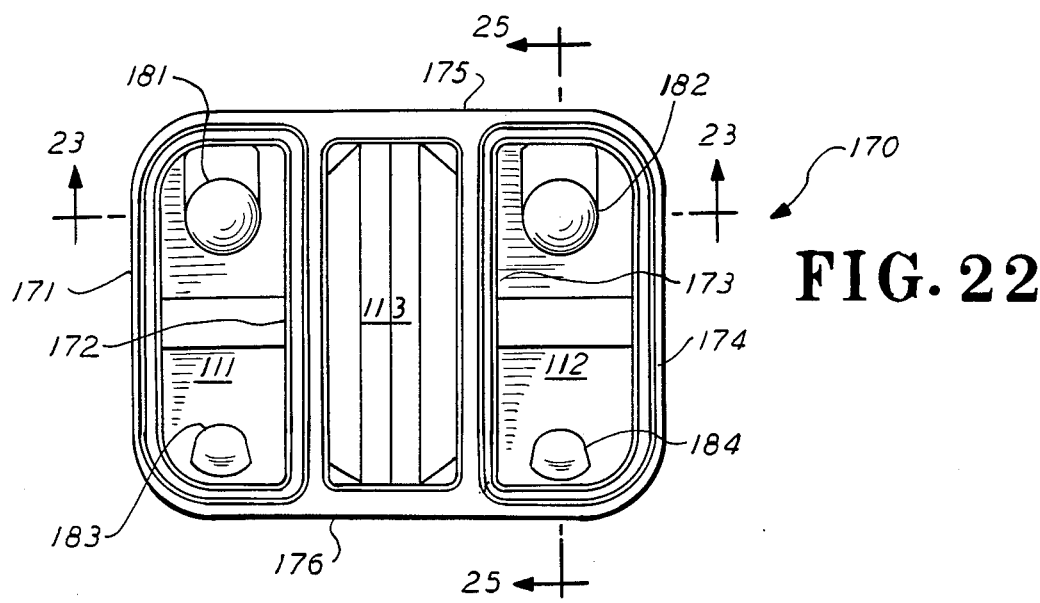
FIG. 22
FIG. 23
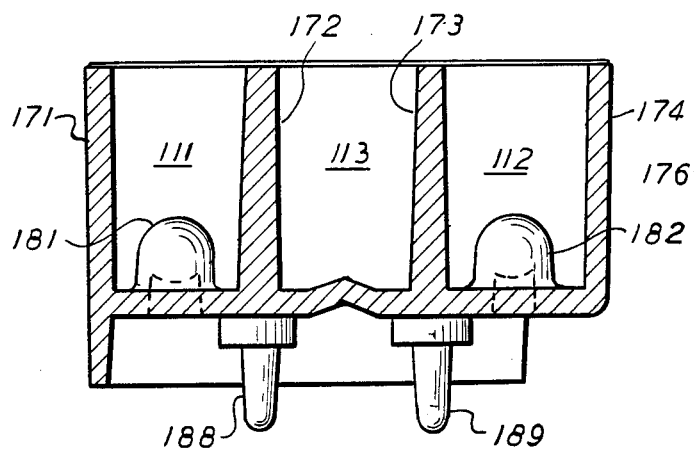
FIG. 25
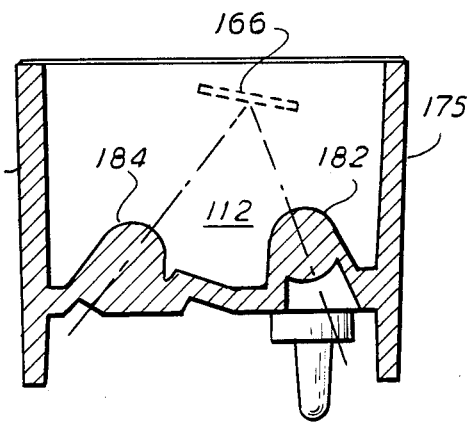
FIG. 24
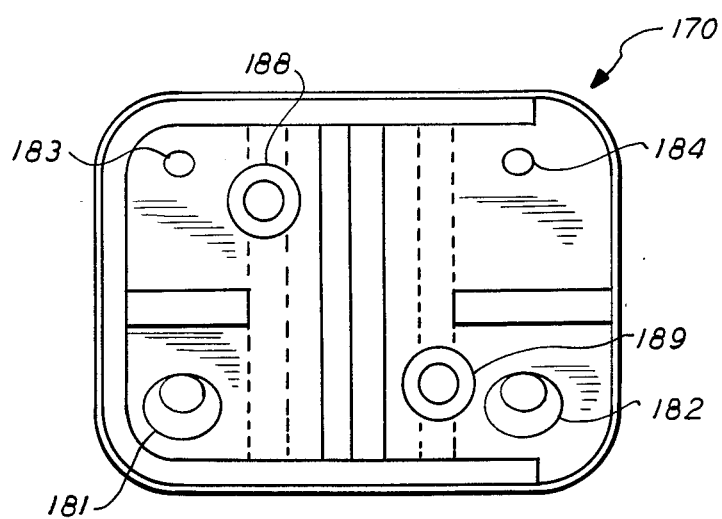

SELF-SUFFICIENT INCUBATION ASSEMBLY

CROSS-REFERENCE TO RELATED APPLICATIONS

This application is a continuation-in-part application of continuation application Ser. No. 411,631, filed Aug. 26, 1982, which was a continuation of parent application Ser. No. 238,049, filed Feb. 25, 1981, both prior applications entitled "Self-Sufficient Incubation Assembly" and both now abandoned.

FIELD OF THE INVENTION

This invention relates generally to the field of microbiology, and more particularly, to a self-sufficient incubation assembly for the in situ or in vitro culture of microorganisms such as bacteria.

BACKGROUND OF THE INVENTION

Detection of microbial pathogens by culture techniques has been routine and customary since the work of Pasteur. The elevation of culture media to physiological temperature range of the organism has been crucial to the development of in vitro microbiological procedures. A broad range of incubators has been devised; the prior art on incubation is directed toward group, or batch incubation in an oven-like apparatus, such as disclosed in U.S. Pat. No. 3,553,426, typical of the general state of the art. Microbiological procedures are also disclosed in U.S. Pat. Nos. 3,616,265, 3,149,054 and 3,874,503.

It is practical in laboratory situations to batch incubate microbiological specimens due to the routine basis of sample gathering. When the basis of specimen testing is occasional and non-laboratory based, such as an early self-diagnostic, the maintenance of an at home incubator is inconvenient.

OBJECTS OF THE INVENTION

It is an object of the present invention to provide a novel incubation assembly.

Another object of the present invention is to provide a novel self-sufficient incubation assembly including nutrient media, heating element and energy sources, etc. for instantaneously initiating and continuing microbiological procedures.

A still further object of the present invention is to provide a novel self-sufficient incubation assembly having an optical assembly to visually magnify the culture growth and thus enhance observation of the microbial colonies.

Still another object of the present invention is to provide a novel disposable self-sufficient incubation assembly.

Yet another object of the present invention is to provide a novel self-sufficient incubation assembly which is relatively small and inexpensively produced.

SUMMARY OF THE INVENTION

These and other objects of the present invention are accomplished by a novel self-sufficient incubation assembly comprised of a base member formed of suitable insulating material and a cover member therefor wherein the base member is formed with a chamber in which is positioned a culture growth dish assembly including a heating element readily connectable to a source of electric energy and wherein nutrient agar cells may be or are readily positioned on the culture growth dish assembly. In a particularly preferred embodiment, the self-sufficient incubation assembly is provided with an optical assembly including a positive magnification lens system to permit observation of the microbial colonies, in enlarged view.

BRIEF DESCRIPTION OF THE DRAWINGS

A better understanding of the present invention as well as other objects and advantages thereof will become apparent upon consideration of the detailed disclosure thereof, especially when taken with accompanying drawings, in which like numerals indicate like parts throughout, and wherein:

FIG. 1 is an isometric view, partially in section, of the incubation assembly of the present invention;

FIG. 15 is a diagrammatical illustration of baselining circuitry of the alternate embodiment of the present invention;

FIG. 16 is a diagrammatical illustration of the electrical circuitry or hybrid circuit of the alternate embodiment of the present invention;

FIG. 17 is a truth table showing the decoder algorithm used in the alternate embodiment of the present invention;

FIG. 22 is a plan view of the bottom of the transparent cuvette of the alternate embodiment of the present invention;

FIG. 23 is a cross-sectional view taken along the line 23—23 of FIG. 22;

FIG. 24 is a bottom view of the transparent cuvette bottom of FIG. 22; and

FIG. 25 is a cross-sectional view taken along the line 25—25 of FIG. 22.

DETAILED DESCRIPTION OF THE INVENTION

Figure 2:
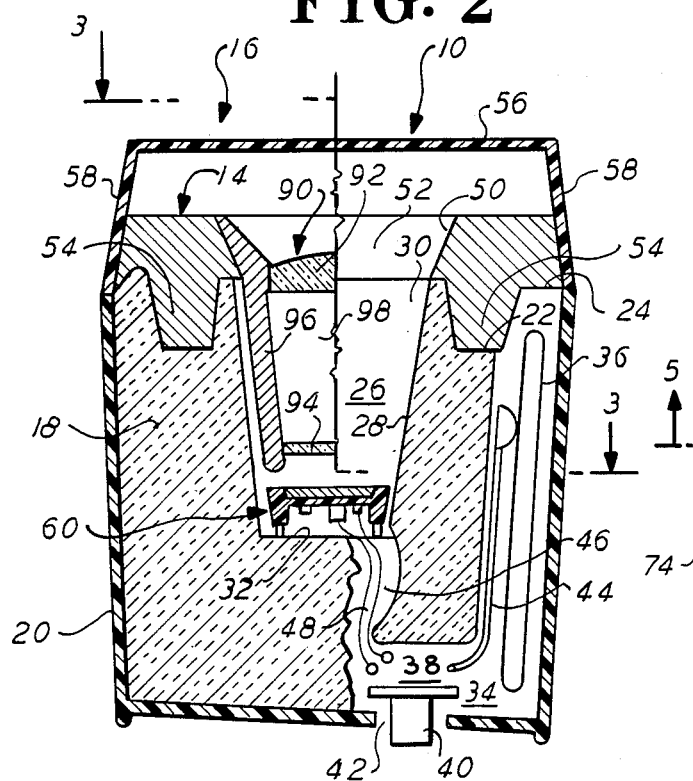
FIG. 2 is a cross-sectional view of the incubation assembly of FIG. 1.
Figure 3:
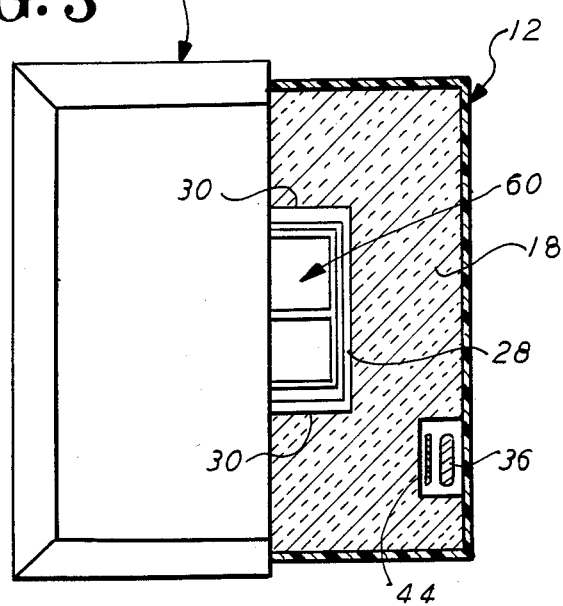
FIG. 3 is a plan view, partially in section taken along the line 3—3 of FIG. 2.

Referring now to FIGS. 1 to 3, there is illustrated a generally square-shaped incubation assembly of the present invention, generally indicated as 10, comprised of base member 12, an inner cover member 14, and a top closure member 16. The base member 12 of the incubation assembly 10 is comprised of a substantially solid body 18 formed of an insulating material, such as closed celled polyurethane, positioned within a hollow container 20 formed of a rigid thermoplastic material to provide structural integrity to the incubation assembly 10. The inner surface of the hollow container 20 may be formed with a vacuum metal-plated surface for heat transfer considerations.

The solid body 18, FIG. 2, is formed with a generally U-shaped (in cross-section) channel 22 circumferentially disposed within a top surface 24 of the solid body 18 to cooperate with the inner cover member 14, as hereinafter more fully disclosed. Within the area defined by the circumferentially disposed, U-shaped channel 22 of the solid body 18, there is formed a centrally disposed, substantially rectangularly shaped inner chamber 26 defined by downwardly and inwardly inclined inner side walls 28 and 30 terminating by a bottom wall 32.

About a side portion of the solid body 18, there is formed a vertically disposed channel 34 forming with the inner surface of the hollow container 20 a housing chamber for a battery generally indicated at 36, such as the planar-type battery manufactured by the Polaroid Corporation. About a bottom portion of the solid body 18, there is formed a horizontally disposed channel 38 for positioning a switch assembly 40 with access thereto being provided by an opening 42 in the bottom of the hollow container 20. The switch 40 is connected by conductors 44 to the battery 36. A channel 46 is provided between chamber 26 and channel 38 for conductors 48.

The generally square shaped inner cover member 14, FIG. 2 is provided with a rectangularly shaped opening formed by downwardly and inwardly sloping walls, 50 and 52, the lower portions of which cooperate with the top portion of the side walls 28 and 30, respectively, defining the chamber 26. The inner cover member 14 is formed with a downwardly extending, circumferentially disposed U-shaped (in cross section) portion 54 cooperating with the U-shaped channel 22 of the solid body 18 to provide for structural integrity and to enhance thermal properties.

The top closure member 16 is formed of a top wall 56 and downwardly depending side walls 58, the ends of which cooperate with the top of the hollow container 20.

Figure 4:
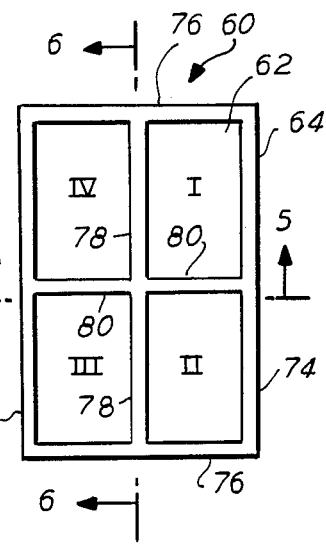
FIG. 4 is a plan view of the culture growth dish assembly.

To permit microbial growth, there is positioned within the lower portion of the chamber 26 a rectangularly shaped culture growth dish assembly generally indicated as 60 (referring now to FIGS. 4 to 6) comprised of thermally conductive plate member 62 formed of a biologically inert coated substrate, such as aluminum or steel, positioned within a plastic frame member 64.

The thermally conductive plate member 62 (FIG. 5) having a top surface 66 and a bottom surface 68 is provided on the bottom surface 68 thereof with heating elements 70 connected to circuitry, generally indicated as 72, comprised of transistors and a thermistor for controlling the temperature to which the heating elements 70 are raised and for maintaining the heating elements 70 at a temperature to provide a physiological temperature range of between about 35.8° to about 36.2° C.

The frame member 64 (FIG. 4) is formed of downwardly and inwardly inclined side walls 74 and end walls 76 including cross members 78 and 80 disposed perpendicularly to one another and intermediate the side walls 74 and end walls 76, respectively, forming cells I to IV with the plate member 62. Beneath a plane formed by the lower portion of the cross member 78 and 80, there is formed a groove 82 (FIGS. 5 and 6) in one end wall 76, a groove 84 in each side wall 74 and a slot 86 in the other end wall 76 for positioning of said plate member within the frame member 64, the slot 86 being dimensioned to permit passage of circuitry 72. Generally the incubation assembly 10 of the present invention is provided with nutrient agar cells 88 (one shown) to permit instantaneous use of the incubation assembly 10.

In a preferred embodiment of the present invention (FIGS. 1 and 2), there is provided an optical assembly for positive magnification, generally indicated as 90, comprised of an upper lens 92 and a lower lens 94 mounted in spaced relationship to one another for a 2-3 × magnification in a lens mounting assembly formed of downwardly and inwardly inclined side walls 96 and end walls 98 substantially in parallel relationship to the inner side walls 28 and 30, respectively, of the chamber 26 of the solid body member 18 to substantially inhibit convective flow of gas within the chamber 26 upon placement of the optical assembly 90 within the chamber 26 of the solid body 18.

In operation, a drop of suspect fluid is placed upon the surface of the agar cell 88 disposed in cell IV of the culture growth dish assembly 60, and the inner cover member 14 including optical assembly 90 is positioned on the base member 12 thereby essentially sealing chamber 26. The switch 40 is placed on an ON mode thereby causing current to flow from the battery 36 to the circuitry 72 and thus the heating element 70 to cause the temperature of the heating elements 70 to be raised to the desired physiological temperature range, i.e. 36° C.±02° for a period, generally for at least 18 hours, adequate for microbial growth and concomitant colony formation useful in enumeration and identification.

While a preferred embodiment of the present invention has been described above, it will be apparent that study of the colony formation may be made by removal of the culture growth dish assembly 60 from the incubation assembly 10 or by removal of a sample therefrom.

Referring now to FIGS. 7 to 18, there is illustrated an alternate embodiment of the self-sufficient incubation assembly of the present invention, embodied in the manner taught in detail below, as a self-sufficient urinary tract infection kit for indicating the presence of a Gram negative infection, a Gram positive infection, or the absence of both. As further known to those skilled in the incubator art, in prior art incubators neither the culture media nor the receptacle for receiving the media, such as a cuvette, is in intimate contact with either the heating element or the means for optical or electro-optical viewing of the microorganism cultivation; such lack of intimacy inherently introducing unwanted loss and distortion into the apparatus. Further, prior art incubators including computation means for computing microorganism cultivation, locate the computation means and the electrical circuitry in which the computation means is embodied outside the area of the incubator where the cuvette or other culture media receptacle is located whereby the heat of operation generated by such circuitry is dissipated and not utilized in the process of culture media heating and microorganism cultivation. Thus, where the incubator is energized by a battery, such as for home use, the dissipation of such heat can be significant because the battery must be sufficiently large, with its attendant expense, to provide the entire energy required for bacterial incubation or cultivation and operation of the external circuitry.

Generally, the alternate self-sufficient incubation assembly of the present invention utilizes an electro-optical methodology of transluminating a bacteria seeded liquid culture medium by means of a light emitter and detector of a photometer which over a given period of time measures or computes the bacterial growth or proliferation by measuring or computing the increase in optical density of the liquid culture medium due to bacterial proliferation, such increase in optical density causing a decrease in the intensity of the transluminating light beam or ray passing through the liquid culture medium. Further, generally, this is accomplished by the utilization of a transparent cuvette which has attached to its base and in intimate thermal and optical contact with it, a hybrid circuit including a monolithic chip which provides the computation means for evaluating the electro-optical output of the emitter and detector pairing necessary to take the electro-optical measurement, three light emitting diodes which in cooperation with the computation means on the chip are illuminated in response to a pre-programmed algorithm, also embodied on the chip, to indicate bacterial proliferation, namely to indicate the presence of a Gram positive urinary tract infection, a Gram negative infection, or the absence of both.

Figure 7:
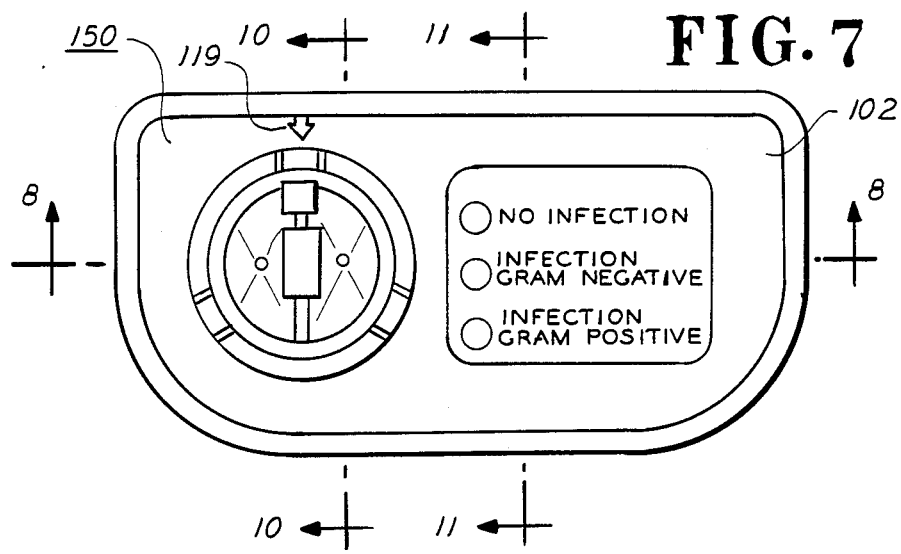
FIG. 7 is a plan view of an alternate embodiment of a self-sufficient incubation assembly of the present invention.
Figure 8:
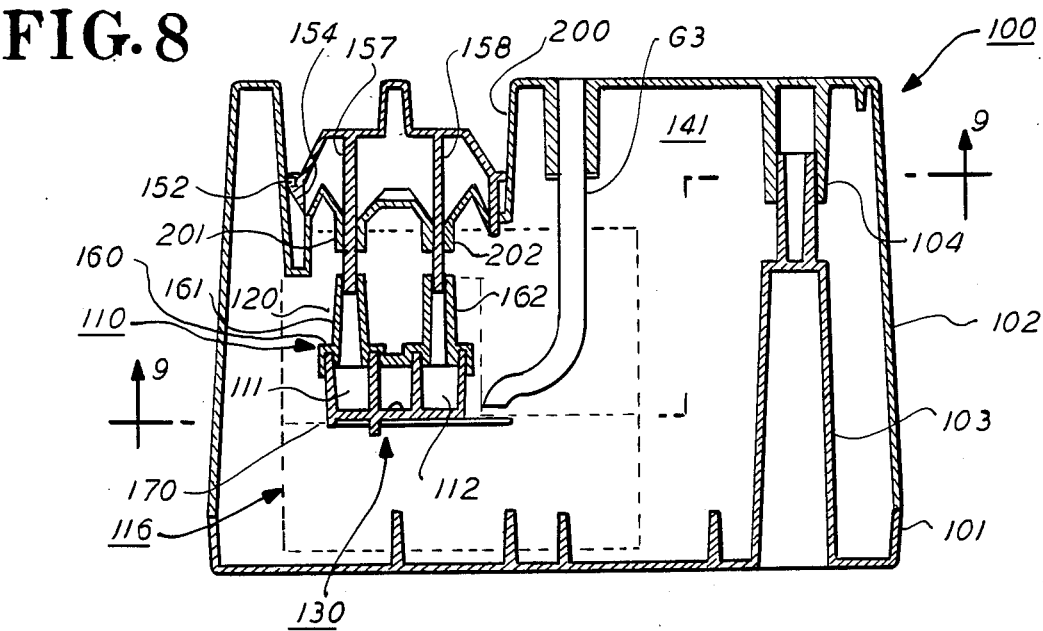
FIG. 8 is a cross-sectional view taken along the line 8—8 of FIG. 7.
Figure 9:
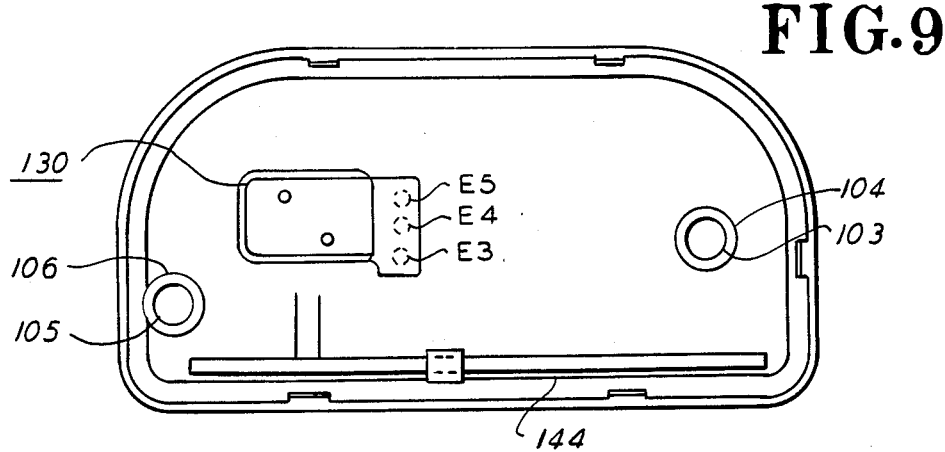
FIG. 9 is an irregular cross-sectional view taken along the line 9—9 of FIG. 8.

Referring now specifically to FIGS. 7–11, and initially to FIG. 8, there is shown an alternate embodiment of self-sufficient incubation assembly of the present invention indicated by general numerical designation 100. The assembly includes a bottom 101 and a top 102, which are essentially shell-like structures, assembled together and provided with required structural rigidity by telescopically interconnecting posts 103 and 104, and posts 105 and 106; posts 103 and 104 being best seen in FIG. 8 and posts 105 and 106 being shown only in FIG. 9 for clarity of invention illustration. The assembly 100 further includes a transparent cuvette 110 providing a first cell 111 and a second cell 112, each cell for receiving a portion of a seeded liquid culture growth medium such as eugonic broth seeded with a urine sample from a urinary tract suspected of having a urinary tract infection such as a Gram negative or Gram positive infection.

Figure 10:
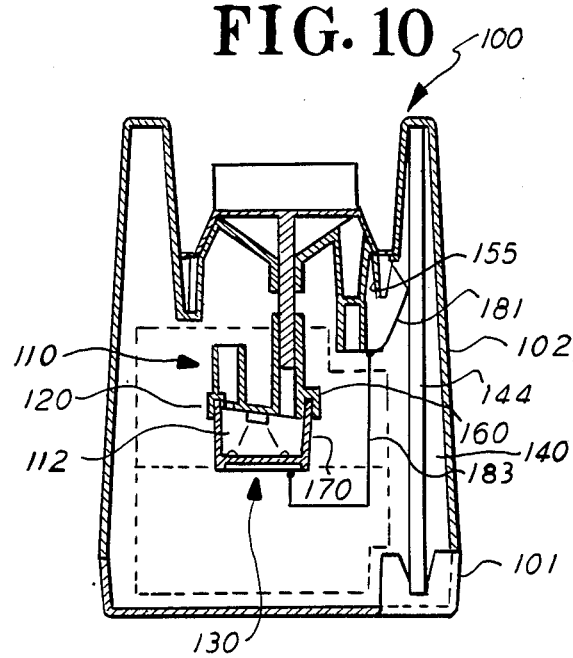
FIG. 10 is a cross-sectional view taken along the line 10—10 of FIG. 7.
Figure 11:
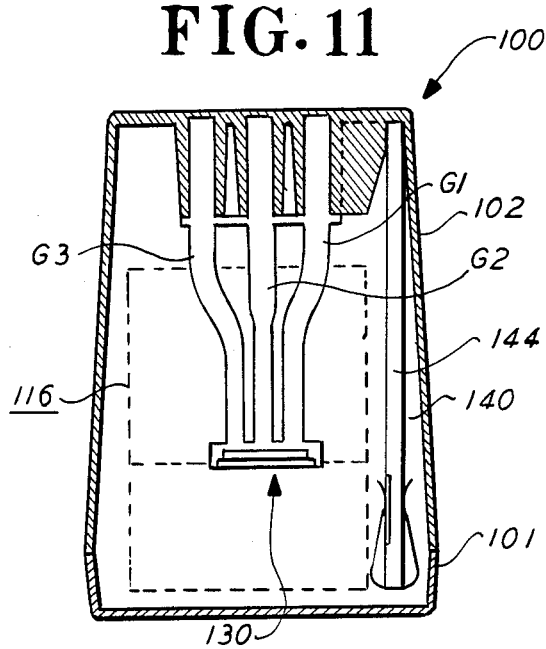
FIG. 11 is a cross-sectional view taken along the line 11—11 of FIG. 7.

The assembly 100 further includes an insulator, of suitable material, indicated by general numerical designation 116 and the two blocks shown in dashed outline in FIGS. 8, 10 and 11; the insulator 116 provides a chamber 120 for receiving the transparent cuvette 110 and insulates the cuvette and seeded liquid culture growth medium received therein during cultivation or incubation. It will be understood that for desired insulation the walls of the chamber 120 for receiving the cuvette 110 must be complementary to the external configuration of the cuvette and such is the case in the present invention, and hence it will be understood that the chamber 120 is coincident with the line defining the exterior of the cuvette and hence no physically distinct chamber 120 is shown. Further, it will be understood that since the cuvette 110 is of irregular configuration, the insulator 116 is made in two pieces, suitably shaped and assembled together, to provide the intimate contact between the insulator and the cuvette for desired insulation.

Electrical circuitry, as indicated by general numerical designation 130, is included and, in accordance with the further teachings of the present invention, is in intimate physical contact with the under side of the transparent cuvette 110 to provide intimate thermal and optical contact between the electrical circuitry and cuvette in accordance with the further teachings of the invention. The electrical circuitry 130, as may be best understood from the diagrammatical illustration of FIG. 16, may include a monolithic chip 132, a film heating resistor 133 for heating the cuvette 110 and seeded culture growth medium received therein to a physiological temperature for the cultivation of microorganisms such as bacteria, a film temperature calibrating resistor 134, a temperature sensing element such as thermistor chip 135 for controlling the heat resistor 133 and thereby controlling to the desired physiological temperature the heat applied to the cuvette and the seeded culture growth medium received therein, a first photoemitter and photodetector pair E1 and D1, a second photoemitter and photodetector pair E2 and D2, and additional photoemitters E3, E4 and E5; it will be understood that upon an understanding of the teachings of the present invention electrical circuitry 130, such as illustrated diagrammatically in FIG. 16, may be readily constructed by those skilled in the art. For example, the substrate 131 may be of a melamine fiberglass base, a porcelainized metal base, or a ceramic substrate. The photoemitters and photodetectors may be suitable available emitter and detector dies suitably bonded to the substrate at appropriate locations as shown; the film resistors may be suitably available such resistors and also suitably deposited on the substrate at appropriate locations as shown; the thermistor chip 135 may be a suitable available semi-conductor thermistor chip suitably bonded to the substrate as shown; and the monolithic chip 132 may be made of any one of several methods known to the prior art and may be made to embody, in combination with the pairs of photoemitters and photodetectors E1 and D1 and E2 and D2, a photometer, such as a turbidity meter, and further embody circuitry for base lining the photometer, temperature monitoring of the cuvette, indicator light illumination of the photoemitters E3, E4 and E5, as well as temperature control of the seeded culture growth medium during cultivation or incubation of the microorganisms or bacteria. The monolithic chip 132 also may be suitably bonded to the substrate 131 and interconnected to the other electrical elements via bonding wires in the manner well known to those skilled in the art. Accordingly, it will be understood that the specific method of manufacture of the electrical circuit 130 is not within the contemplation of the present invention but that such circuitry, upon an understanding of the teachings of the present invention, may be manufactured by any one of several methods well known to those skilled in the art, and upon being so manufactured, embodies a portion of the present combination invention.

The alternate embodiment also includes an optical system for providing an external indication of the growth of the microorganisms or bacteria within the closed interior of the self-sufficient incubation assembly. In this embodiment, this may be best understood by reference to FIGS. 11 and 16, three electro-optical guides G1, G2 and G3 are in physical and electrooptical registration and communication with the photoemitters E3, E4 and E5, respectively, and communicate illumination emanating from these photoemitters to the exterior of the assembly to provide an external visual indication of the detection of growth of microorganisms or bacteria deep within the closed exterior of the assembly. The electro-optical light guides G1, G2 and G3 may be supported and positioned, for example, by suitable complementary shaped guideways formed in the insulator 16.

Figure 20:
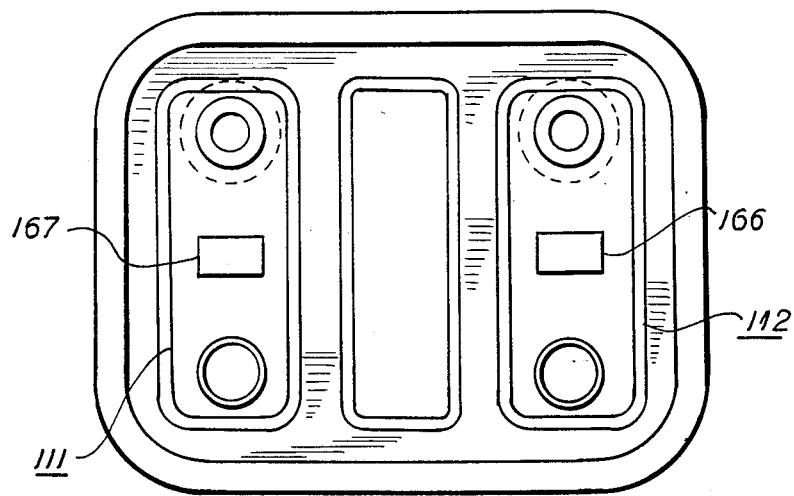
FIG. 20 is a bottom view of the transparent cuvette of FIG. 18.

Referring now more specifically to the structure of the transparent cuvette 110, as may be noted generally from reference to FIGS. 8 and 10, the cuvette is comprised of a top 160 and a bottom 170 each made of suitable transparent material, such as a suitable transparent moldable plastic, and adhered together by a suitable adhesive or bonding operation; the irregular configuration and closed container aspect of the cuvette 160 require, for cost and convenience of manufacture, that it be made in two pieces, namely the top 160 and bottom 170 and thereafter assembled. Referring specifically to FIGS. 18–21 and the specific structure of the cuvette top 160, it will be noted that the top is provided with a pair of upwardly extending intake or entrance galleries 161 and 162 and a pair of shorter and upwardly extending exiting or venting galleries 163 and 164. It will be understood that entrance gallery and venting gallery 161 and 163 are associated with cuvette cell 111 and that entrance gallery 162 and venting gallery 164 are associated with cuvette cell 112; hence, the entrance gallery 161 and venting gallery 163 operate as a pair and the entrance gallery 162 and venting gallery 164 operate as a pair. As may be best understood by reference to FIG. 21, and with regard to cell 112, the upper surface of the cell, provided by the lower surface 165 of the top 160, is inclined or angled to insure venting upon filling of the cell with a seeded culture growth liquid medium and in a manner explained in detail later, reflector 166, such as a strip of shiny metal or tape or other suitable surface treatment, is suitably adhered to the top 165 to reflect light from the photoemitter E2 to the photodetector D2; it will be understood that cell 111 is also provided with an inclined top and a reflector 167 as shown in FIG. 20; the reflector 167 is for reflecting light from the photoemitter E1 to the photodetector D1.

The cuvette bottom 170, as shown in detail in FIGS. 22–25, is provided with a plurality of integrally formed, upwardly extending walls 171–176 defining cuvette cells 111–112 and the space 113 therebetween. The bottom 170 further includes upwardly extending integrally formed meniscus collimating lens 181 and 182 and integrally formed meniscus collecting lens 183 and 184. It will be understood that collimating lens 181 and collecting lens 183 are associated with cuvette cell 111 and hence operate as a pair and that collimating lens 182 and collecting lens 184 are associated with cuvette cell 112 and hence operate as a pair; it will be still further understood that collimating lens 181 and collecting lens 183 operate or function in cooperation with reflector 167 and that collimating lens 182 and collecting lens 184 operate or function in cooperation with reflector 166, as shown in FIG. 25. As is further shown in FIG. 25, the respective axes of the collimating and collecting lens 182 and 184 are disposed at suitable angles with respect to the reflector 166 (shown in dashed outline but shown where the reflector 166 is positioned upon assembly of the cuvette top and bottom) such that a beam or ray of light collected by lens 182 from photoemitter E2 is focused on the reflector 166 and the reflector reflects the received light along the axis of the collimating lens 184 to the photodetector D2, similarly with regard to collimating and collecting lens 181 and 183, reflector 167 and photoemitter E1 and photodetector D1. The bottom 170 is provided with locating pins 188–189 to establish proper registration of the cuvette 110 with the electrical circuitry 130.

Figure 12:
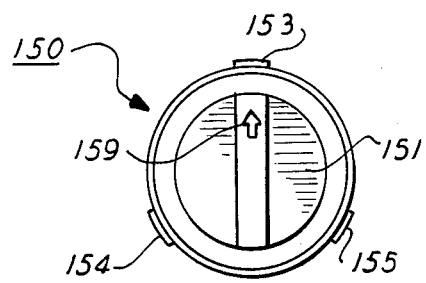
FIGS. 12, 13 and 14 are, respectively, plan, side and bottom views of a cap of the alternate embodiment of the present invention.
Figure 13:
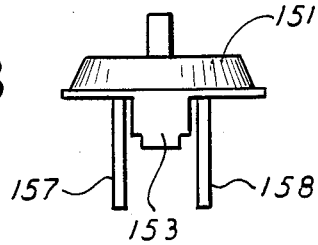
Figure 14:
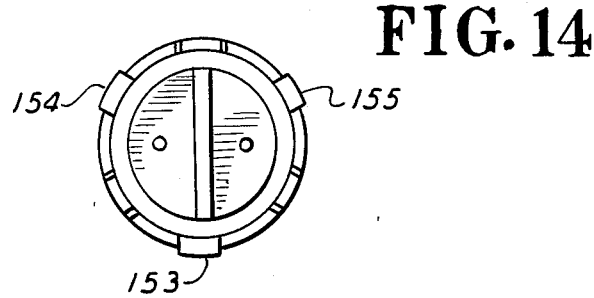
Figure 18:
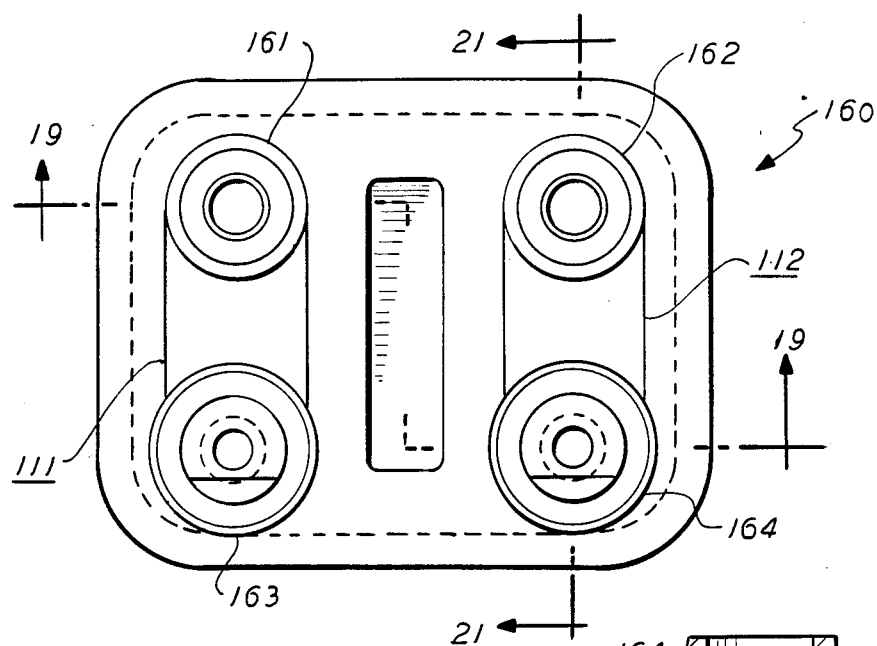
FIG. 18 is a plan view of the top of a transparent cuvette of the alternate embodiment of the present invention.
Figure 19:
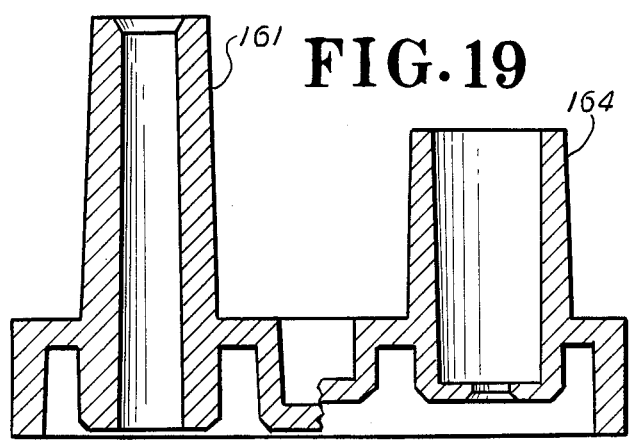
FIG. 19 is an irregular cross-sectional view taken along the line 19—19 of FIG. 18.
Figure 21:
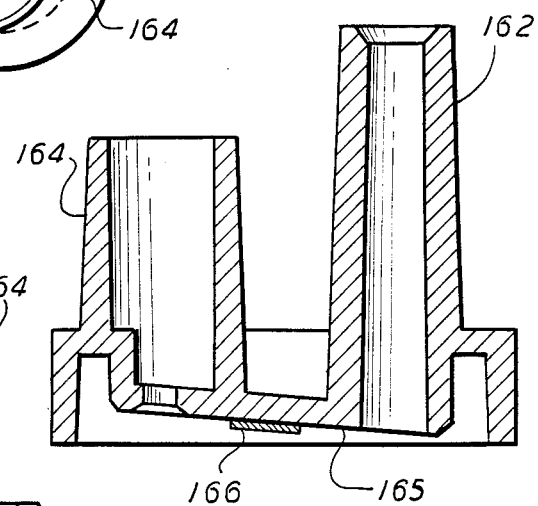
FIG. 21 is a cross-sectional view taken along the line 21—21 of FIG. 18.

The self-sufficient incubation assembly of the present invention further includes a cap indicated by general numerical designation 150 and which cap is shown in detail in FIGS. 12–14. Generally, cap 150 has a dual function, namely it seals or closes the cuvette 110 upon a seeded liquid culture growth medium being received therein for microorganism cultivation and also interconnects the electrical circuitry 130 with the battery 144. Specifically, and referring to FIGS. 12–14, the cap includes a top 151, a plurality of radially disposed and downwardly extending members 153, 154 and 155 for being received in correspondingly radially disposed and downwardly extending slots formed in the top 102 of the assembly 100 as may be best seen in the upper lefthand portion of FIG. 8. Additionally, the cap 150 is provided with a pair of downwardly extending plug members 157 and 158 for respectively entering and sealing the entrance galleries 161 and 162 as is also shown in FIG. 8. It will be further understood that the cap 150 has two positions, the first position with the arrow 159 of the cap (FIG. 12) not aligned with the arrow 119 provided on the top of the assembly as shown in FIG. 7 and in this position the cap does not interconnect the electrical circuitry 130 with the battery 144 and the cap is not locked to the assembly 100. However, upon the seeded liquid culture medium being placed in the cuvette 110 and operation of the assembly being desired, the cap is rotated 180° to align the arrows 159 and 119 and the cap is inserted into the top portion of the assembly whereupon the plug members 157 and 158 seal the entrance galleries 161 and 162 and the downwardly extending member 154, as shown in FIG. 8, is provided with an inwardly extending slot or groove which is engaged by the outwardly extending resilient member 152, as shown, to lock the cap 150 to the top 102 of the assembly 100 to close and seal the assembly for incubation. Additionally, upon the arrows 159 and 119 being aligned and the cap inserted into the top of the assembly, the downwardly extending member 155, as may be best seen in FIG. 10, engages a spring mounted electrical connector 181 to force the connector into engagement with the battery 144 to interconnect the battery 144 through the electrical connector 183 to the electrical circuitry 130 to energize the circuit and commence incubation.

Referring again to FIG. 8, and to the upper lefthand portion, it will be understood that the top 102 is formed inwardly to provide a receptacle 200 which is provided at its bottom with an integrally molded pair of funnels 201 and 202 aligned vertically with the entrance galleries 161 and 162 of the cuvette 110.

The operation of the alternate embodiment self-sufficient incubation assembly 100 of the present invention will now be set forth embodied as a urinary tract infection kit although it will be understood by those skilled in the art that the present invention is not so limited but is of general use with regard to the cultivation of microorganisms such as bacteria. As is further known to those skilled in the art, bacteria can be classified into two groups, Gram negative and Gram positive bacteria. As is further known to those skilled in the art, urinary tract infection is caused primarily by Gram negative bacteria such as E. coli; however, as is also known, urinary tract infection can be caused by Gram positive bacteria. While virtually all sampled urine contains some bacteria, the levels of bacteria of concern are those levels which are referred to in the art as clinically relevant levels of bacteria, for example, 100,000 bacteria per ml, and it is the early detection of the presence of such clinically significant levels of bacteria that is the purpose of urinary tract infection detection apparatus in order that appropriate antibiotics can be prescribed and taken before the onset of a virulent bacterial infection.

As is further known to those skilled in the art, Gram negative bacteria reproduce faster than Gram positive bacteria, Gram negative bacteria reproducing approximately every 20 minutes while Gram positive bacteria reproduce approximately every 40 minutes, that is at approximately one half the rate of Gram negative bacteria. Hence, with this reproduction information, bacteria in a urine sample from a urinary tract suspected of having an infection may be cultivated at a physiological temperature, such as for example 37° C. or 98.6° F., for a given period of time such as for example approximately four hours, and the bacteria level present at the beginning of the period per ml may be compared with the bacteria present per ml at the end of the period and the presence or absence of a clinically significant level of bacteria can be determined. In addition, by knowing the respective reproduction rates of Gram negative and Gram positive bacteria, and by comparing the respective growths of such bacteria over the time interval, the logical determination of the presence of a Gram negative infection or of a Gram positive infection can also be determined or clinically inferred.

As is further known to those skilled in the art, the growth of bacteria in a sample, such as a seeded liquid culture growth medium, over a given period of time can be determined or measured by the use of a photometer such as a turbidity meter. At the beginning of the time interval, the optical density of the sample can be measured by passing a transluminating beam or ray of light through the sample and the energy loss due to light scattering of the beam can be measured and recorded. Bacteria, as is known, upon growth or reproduction scatters light and as bacteria in the sample reproduce or proliferate such as in response to cultivation, more light is scattered thereby further increasing the optical density of the sample and hence at the end of the time interval the transluminating beam or ray can again be passed through the sample and the increased energy loss caused by increased optical density or light scattering can again be measured and compared vis-a-vis the earlier measurement. The difference in energy level of the light beam can be used, empirically, and particularly knowing the reproduction rate of the bacteria present, to provide a measurement of bacteria growth in the sample over the time interval. It will be further understood that circuitry embodied in the monolithic chip 132 and the photoemitter and photodetector pairs E1–D1 and E2–D2, in combination with the collimating and collecting lens and reflectors of the transparent cuvette 110 function as a photometer or turbidity meter.

Referring now specifically to the operation of the present invention when embodied as a urinary tract infection kit, it will be presumed that a urine sample has been taken from a urinary tract suspected of having a urinary tract infection, that the urine sample has been diluted in a suitable liquid culture growth medium, such as eugonic broth, to seed the broth, that the cap 150 of the assembly 100 has been removed, and that the seeded liquid culture growth medium has been poured into the receptacle 200 where it flows through the two funnels 201, 202 where it substantially divides and enters into the cells 111 and 112 of the transparent cuvette 110. It will be understood that cell 111 has been preconditioned to grow only Gram positive bacteria by having a Gram negative inhibitor placed therein such as by coating the walls of cell 111 with sodium azide powder which, as known to those skilled in the art, inhibits the growth of virtually all Gram negative bacteria. However, cell 112 has not been so preconditioned and hence both Gram negative and Gram positive bacteria will grow in cell 112. The cap 150 will then be placed into the receptacle 200 with the arrows 119 and 159 aligned to initiate operation of the assembly by energization of the electrical circuit 130 as taught above. It will be understood that the monolithic chip 132 of the electrical circuitry 130, FIG. 16, may have a suitable circuit embodied therein to cause all of the photoemitters E3, E4 and E5 to be temporarily activated, or activated in a predetermined sequence, to provide indication to the user that the self-sufficient incubation assembly is functioning; thereafter such photoemitters will be extinguished and bacteria cultivation commenced and continued for a time interval.

As is further known to those skilled in the art, to provide significant turbidity measurements at the beginning and end of the time interval, the photometer or turbidity meter must be baselined to provide appropriate measurement references against which future measurements may be measured or compared for significant results. Accordingly, the electrical circuitry 130 of the present invention, in accordance with the following further teachings, may be suitably baselined for significant measurements. Referring to FIG. 15, there is shown such baselining circuitry, indicated by general numerical designation 220, which may be used in accordance with the teachings of the present invention and which baselining circuitry, although illustrated as a block diagram in FIG. 15, will be embodied in the monolithic chip 132 of FIG. 16 in a manner known to those skilled in the art. The baselining circuitry 220 is a dual channel circuit including channel 230 associated with cuvette cell 111 and channel 240 associated with cuvette cell 112. Channel 230 includes the series connection of the photoemitter E1, photodetector D2, amplifier A1, switching network S1, threshold comparator T1, start-stop logic 232, counter 234, digital to analog converter 236 and amplifier A2; similarly, the channel 240 includes the series connected components as shown. Additionally, the baselining circuit includes the threshold comparators T3 and T4 connected to the decoder 250 which in turn is provided with three outputs as shown, for providing one of three binary outputs indicative of the bacterial conditions shown, namely no infection, Gram negative infection, or Gram positive infection.

Continuing from above, it will again be presumed that the circuitry 130 has been energized by the battery 144 due to the closure of the cap 150 and now the operation of the baselining circuitry 220 and the decoder 250 for providing the bacterial infection indication shown will be described. With regard to baselining channel 230, upon energization the switching network SW1 assumes state S1 whereupon photoemitter E1 has no output and photodetector D1 has no input and therefore no output; this lack of output will be reflected to amplifier A1 and threshold comparator T1 will signal the start-stop logic 232 to initiate counting which is then converted, digital to analog by the converter 236, deboosted by amplifier A2, and reflected in a gradually increasing light level emanating from the photoemitter E1. At such time the evoked response of the photodetector D1 reaches the preset level of threshold detector T1, the start-stop logic is signalled to stop counting thus freezing the output level of the photoemitter E1 and channel 230 is now baselined; similarly, channel 240 is also baselined to the preset level of threshold detector T2. At the conclusion of the cultivation time interval, for example approximately four hours, which time elapse is built into the circuitry of the monolithic chip 132 in a manner known to those skilled in the art, the switching network SW1 assumes state S2 and the evoked response of the photodetector D1 in response to the output of the photemitter E1 transluminating the cuvette cell 111 is connected through amplifier A1 to threshold comparator T3 and compared with its preset threshold level and if the later evoked response of the photodetector D1 falls below the threshold of threshold comparator T3 a binary 0 signal is transmitted to the decoder 250 to indicate the absence of clinically significant Gram positive bacteria growth in cell 111. However, if the evoked response of the photodetector D1 is at least equal to or greater than the preset threshold of threshold comparator D3, a binary 1 signal is transmitted to the decoder 250 to indicate the presence of clinically significant Gram positive bacteria growth in cell 111. Similarly, threshold comparator T4 is preset to send a binary 0 or 1 signal to the decoder 250 to respectively indicate the absence of clinically significant levels of Gram negative and/or Gram positive bacteria growth in cell 112 or the presence of clinically significant levels of Gram negative and/or Gram positive bacterial growth in cell 112. It will be understood that the preset threshold levels of the respective threshold comparators will be preset empirically and in accordance with the recognized respective reproduction and growth rates of Gram positive and Gram negative bacteria, for example the preset threshold of threshold comparator T4 of channel 240 will be approximately twice the preset level of threshold comparator T3 of channel 230 since it is known that Gram negative bacteria grow at approximately twice the rate of Gram positive bacteria. The decoder 250, will interpret or decode the binary 1 or 0 signals received from the respective threshold comparators T3 and T4 to provide an indication of bacterial growth in accordance with the algorithm, sometimes referred to in the art as a truthtable, set forth in FIG. 17. It will be further understood that the algorithm or truthtable of FIG. 17 will also be embodied in suitable circuitry included in the monolithic chip 132 of the electrical circuit 130.

Referring now to the decoder algorithm of FIG. 17, upon the decoder 250 of FIG. 15 receiving the binary 1 from the output of cell 111 and a binary 0 from the output of cell 112, this will be interpreted and the appropriate photoemitter E4 illuminated to indicate the presence of clinically significant levels of Gram positive bacteria in the urine sample. Upon the decoder receiving a binary 0 from cell 111 and a binary 1 from cell 112, this will be interpreted by the decoder 250 to indicate the presence of clinically significant levels of Gram negative bacteria and photoemitter E4 will be illuminated to provide such indication. Should a binary 0 be received from both cells, this will be decoded to indicate the absence of any clinically significant infection and photoemitter E3 will be illuminated to provide such visual indication. However, it is possible for the decoder to receive a binary 1 from both cell 111 and cell 112 and, as indicated in FIG. 17, this is interpreted or decoded by the decoder 250 to indicate the presence of clinically significant levels of Gram positive bacteria. This results from one of two possible situations and the following logic: one possibility is that Gram positive bacteria were present in such large quantity or experienced such large growth during cultivation as to exceed both the preset threshold level of threshold comparator T3 of the Gram positive cell 111 and the preset threshold level of the threshold comparator T4 of the Gram positive and/or Gram negative bacteria cell 112; the other possibility is that there were mixed bacteria present, indicating the possibility of a mixed infection, and that the growth of the Gram positive bacteria in cell 112 exceeded the threshold of threshold comparator T3 and that there was either mixed or Gram negative bacteria growth in cell 112 sufficient to exceed the preset threshold of threshold comparator T4. In such event, as known to those skilled in the art, treatment for Gram positive bacteria or Gram positive infection is indicated.

Figure 5:
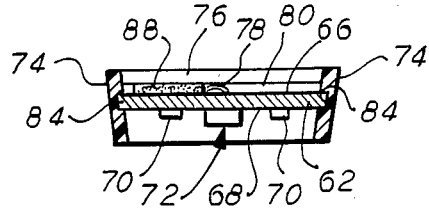
FIG. 5 is a cross-sectional view taken along the line 5—5 of FIG. 4.
Figure 6:
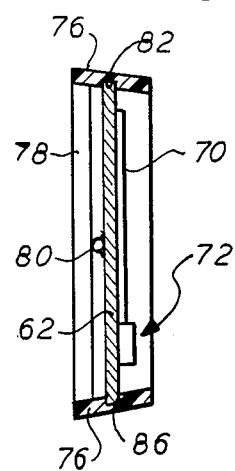
FIG. 6 is a cross-sectional view taken along the line 6—6 of FIG. 4.

It will be noted from FIGS. 8, 10 and 11, and from FIG. 16 where cuvette 110, cell 111 and cell 112 are shown in dahsed outline, and in accordance with the teachings of the present invention, that the electrical circuitry 130 and the temperature control element 135 are in intimate physical contact with the cuvette 110 specifically the underside thereof. Hence, the temperature of the temperature control element 135 will be substantially the same as the temperature of the cuvette and the seeded culture growth medium contained therein whereby improved temperature control of the medium is provided, and the heat of operation of the electrical circuitry 130 will supplement the heat applied by the heating resistor 133 and battery 144 to the cuvette 110 and the seeded culture growth medium received therein whereby the energy required to be supplied by the battery 144 will be less than would be required were the electrical circuitry 130 to be located externally of the cuvette and not in intimate physical contact therewith. Identically, in the earlier embodiment of FIGS. 1–6, since the electrical circuitry 72 and the temperature control thermistor included therein are in intimate physical contact with the culture growth dish assembly 60 as shown in FIGS. 5 and 6, specifically the underside thereof, the improved temperature control of the nutrient agar cell is also provided and the heat of operation of the electrical circuitry 72 also supplements the heating of the agar cell by the battery 36.

Referring again to FIG. 16, it will be understood that the photoemitter E1 of FIG. 16 is positioned at the proper point along the optical axis of the collimating lens 181 of the cuvette 110 to maximize collimation of the light emitted by the photodetector for transluminating the culture growth medium received by cuvette cell 111 and the photodetector D1 of FIG. 16 is positioned along the optical axis of the collecting lens 183 to maximize the collection of the light transluminating the culture growth medium and exiting the cuvette 110 for photometric measurement.

It will be be further understood by those skilled in the art that many modifications and variations of the present invention may be made without departing from the spirit and the scope thereof.

What is claimed is:

1. Self-sufficient incubation assembly for the in vitro cultivation of microorganisms, comprising an incubation assembly containing a:

transparent cuvette for receiving seeded fluid culture growth medium seeded with said microorganisms, said cuvette comprising a cell for receiving said seeded fluid culture growth medium and including integrally formed collimating lens, integrally formed collecting lens and reflecting means;

insulating means within the interior of said assembly providing a first chamber for receiving said transparent cuvette;

heating means in continuous actual contact with said transparent cuvette and for heating said transparent cuvette and said seeded fluid culture growth medium;

means providing a second chamber for receiving a self-contained energy source;

electrical circuitry interconnecting said heating means with said energy source and for controlling the temperature of said heating means to cause said heating means to heat said transparent cuvette and said seeded fluid culture growth medium to a predetermined physiological temperature to cultivate said microorganisms, said electrical circuitry including a temperature control element for sensing the temperature of said heated seeded fluid culture growth medium, said electrical circuitry and said temperature control element in continuous actual physical contact with said transparent cuvette to cause the temperature of said temperature control element to be substantially the same as the temperature of said heated seeded fluid culture growth medium, said electrical circuitry further including a photoemitter for producing a transluminating ray, a photodetector for receiving said transluminating ray, computation means and indicating means;

said photoemitter in continuous actual physical contact with said collimating lens and said photodetector in continuous actual physical contact with said collecting lens, said reflecting means and said collimating lens and said collecting lens mutually disposed such that said collimating lens collimates said transluminating ray and directs said ray through said seeded fluid culture growth medium to said reflector which reflects said ray through said seeded fluid culture growth medium to said collimating lens, said culture of said microorganisms reducing the energy level of said transluminating ray upon passing through said seeded fluid culture growth medium and said computation means computing said reduced energy level to activate said indicating means to provide an indication of the reduced energy level of said transluminating ray and thereby the culture of said microorganisms; and optical means in communication with said first chamber and the exterior of said assembly and for providing external to said assembly visual indication of the growth of said microorganisms within the interior of said assembly.

2. Self-sufficient incubation assembly for the in vitro cultivation of seeded fluid culture growth medium including Gram negative bacteria and/or Gram positive bacteria, comprising an incubation assembly containing a:

transparent cuvette providing a first cell for receiving a first portion of said medium and for cultivating Gram positive bacteria, and providing a second cell for receiving a second portion of said medium and for cultivating Gram negative bacteria or Gram negative and Gram positive bacteria, respective growth of said bacteria in said cells providing respective changes in optical densities of said first and second portions of said medium, said transparent cuvette including two pair of integrally formed collimating lens and collecting lens and each pair of lens associated with one of said cells, said transparent cuvette provided with first and second reflecting means and each reflecting means associated with one of said cells and one of said pair of lens, said collimating lens and collecting lens of each pair disposed at respective angles with respect to said associated reflecting means;

insulating means within the interior of said assembly for providing a first chamber for receiving said transparent cuvette;

heating means in continuous actual contact with said transparent cuvette for heating said transparent cuvette and said medium;

means providing a second chamber for receiving a self-contained energy source;

electrical circuitry interconnecting said heating means with said energy source and for controlling the temperature of said heating mean to cause said heating means to heat said transparent cuvette and said medium to a predetermined physiological temperature to cultivate said bacteria, said electrical circuitry including a temperature control element for sensing the temperature of said heated medium, said electrical circuitry and said temperature control element in continuous actual physical contact with said transparent cuvette to cause the temperature of said temperature control element to be substantially the same as the temperature of said heated medium, said electrical circuitry further including photometer means, computation means including decoder means and indicating means;

said photometer for providing first and second light beams for respectively transluminating said first and second portions of said medium and for detecting respective changes in said optical densities over a predetermined period of time by detecting respective changes in the respective intensities of said light beams caused by said changes in optical densities and said decoder means for comparing said respective changes in optical densities in accordance with a predetermined algorithm to determine the presence of clinically significant levels of Gram positive or Gram negative bacteria in said medium or the absence of clinically significant levels of both bacteria in said medium, said photometer means including two pair of photoemitters and photodetectors, each pair of photoemitters and photodetectors associated with one of said cells and each photoemitter being in continuous actual physical and optical contact with one of said collimating lens and each phtotdetector being in continuous actual physical and optical contact with one of said collecting lens, each photoemitter for producing one of said light beams and each collimating lens for receiving one of said light means and directing the beam to the associated reflecting means which reflects the beam to the associated collecting lens;

said indicating means for providing repective indications of said respective clinically significant levels of bacteria in accordance with said determination of said decoder means; and optical means in communication with said first chamber and the exterior of said assembly for providing external to said assembly visual indication of the growth of said bacteria within the interior of said assembly.

3. self-sufficient incubation assembly according to claim 2 wherein said electrical circuitry further includes base lining circuitry including:

first means for establishing a first optical density base line for said first portion of said medium at a first predetermined time;

second means for establishing a second optical density base line for said second portion of said medium at a second predetermined time;

third means for establishing a first optical density threshold for said first portion of said medium and for providing a first binary signal indicative of whether the optical density of said first portion of said medium at a third predetermined time is below or at least equal to said first threshold;

fourth means for establishing a second optical density threshold for said second portion of said medium and for providing a second binary signal indicative of whether the optical density of said second portion of said medium at a fourth predetermined time is below or at least equal to said second threshold; and wherein said decoder means receives and decodes said first and second binary signals in accordance with said predetermined algorithm and provides one of three binary outputs each indicative of one of said clinically significant levels of bacteria.

4. Self-sufficient incubation assembly according to claim 2 wherein said indicating means comprise three photoemitters each connected to said decoder means and each for being illuminated in response to one of said three binary outputs and wherein said optical means comprise three optical light guides each in optical communication with one of said photoemitters.

* * * * *